(12) United States Patent
Sulur et al.

(10) Patent No.: US 8,748,640 B2
(45) Date of Patent: Jun. 10, 2014

(54) PROCESS TO MAKE FUSIDIC ACID CREAM

(76) Inventors: Vanangamudi Subramaniam Sulur, Chennai (IN); Madhavan Srinivasan, Chennai (IN); Neelakandan Narayanan Chulliel, Chennai (IN); Haridas Sankar, Mumbai (IN)

(*) Notice: Subject to any disclaimer, the term of this patent is extended or adjusted under 35 U.S.C. 154(b) by 326 days.

(21) Appl. No.: 13/201,627

(22) PCT Filed: Feb. 16, 2010

(86) PCT No.: PCT/IB2010/050685
§ 371 (c)(1),
(2), (4) Date: Aug. 16, 2011

(87) PCT Pub. No.: WO2010/095091
PCT Pub. Date: Aug. 26, 2010

(65) Prior Publication Data
US 2011/0301138 A1    Dec. 8, 2011

(30) Foreign Application Priority Data

Feb. 18, 2009    (IN) .......................... 358/MUM/2009

(51) Int. Cl.
*C07J 13/00*    (2006.01)
*A61K 9/00*    (2006.01)
*A61K 9/06*    (2006.01)

(52) U.S. Cl.
USPC .......................................... 552/530; 424/400

(58) Field of Classification Search
USPC .......................................... 552/530; 424/400
See application file for complete search history.

*Primary Examiner* — Barbara P Badio

(57) ABSTRACT

The invention discloses a process to make dermaceutical cream containing Fusidic acid which is formed in situ from Sodium Fusidate as the starting raw material, wherein Sodium Fusidate is converted into Fusidic acid under oxygen-free environment created using inert gas, preferably nitrogen. The cream produced by the process of the present invention has greater shelf-life stability and the finer particle size of the API than the conventional creams containing Fusidic acid. The cream produced by the process of the present invention contains Fusidic acid as the API that has been formed in situ from Sodium Fusidate, in a cream base comprising a preservative, an acid, a co-solvent, an emulsifier and a waxy material along with water, preferably purified water. The cream produced by the process of the present invention further optionally contains an ingredient selected from a group comprising, a buffering agent, an anti oxidant, a chelating agent, and a humectant, or any combination thereof.

15 Claims, No Drawings

PROCESS TO MAKE FUSIDIC ACID CREAM

CROSS-REFERENCE TO RELATED PATENT APPLICATIONS

The present application is the U.S. National Stage of International Application No. PCT/B2010/050685, filed on Feb. 16, 2010, and published in the English language on Aug. 26, 2010 as international Publication No. WO 2010/095091, which International Application claims the benefit of priority to Indian National Application No. 358/MUM/2009, filed on Feb. 18, 2009.

FIELD OF INVENTION

The present invention relates to primary and secondary bacterial skin infections and in particular it relates to the process of making a cream useful in the treatment of these infections, said cream incorporating Fusidic acid that has been created in situ using Sodium Fusidate as the starting Active Pharmaceutical Ingredient (API).

BACKGROUND OF INVENTION

Numerous treatments, both topical and systemic, are available for the primary and secondary skin infection caused by sensitive Gram +ve organisms such as *Staphylococcus aureus, Streptococcus* spp etc. Topical and systemic bacterial infection treatment compositions typically employ at least one active pharmaceutical ingredient (API) in combination with a base component. In the cream form, the APIs typically comprise an antibiotic/antibacterial such as Fusidic acid and the like.

In the currently available Fusidic acid creams, Fusidic acid in fine powder form is used as source API. The small particle size enhances its dermal contact by providing a large specific surface area and penetration, and provides a smooth feel on application to skin. However, a serious shortcoming of the fine size of Fusidic acid particles is that it presents an enormous surface area for contact and reaction with molecular Oxygen during manufacture, handling, and processing of the cream. This has serious implications to its chemical stability and results in rapid reduction in potency of the API (Fusidic acid) in the final cream formulation. Degradation due to oxidation is a major cause of instability of currently available Fusidic acid creams. Table 1 show that the degradation in the API samples (Fusidic acid) exposed to oxygen ranged between 7.7% and 11% for conditions ranging from room temperature to 45° C. when analysed at three months of exposure period at the above conditions.

It is known that greater the exposure time of Fusidic acid as the raw API to Oxygen, greater the limitations on stabilising Fusidic acid in a formulation. However, there is no published data on the stability of Fusidic acid over a period of time.

As an alternative to Fusidic acid, Sodium Fusidate is known to have been used to make dermaceutical medicaments for topical application. However, these are in the form of ointment rather than cream. Drawbacks of ointments over creams are well known and it's generally preferable to use creams rather than ointments for topical application.

Several aspects of Fusidic acid as an API are known:
- It is thermolabile
- It is available in cream formulations
- It can be obtained from Sodium Fusidate by dissolving the latter in an aqueous phase and adding acid to the solution, whereby Fusidic acid precipitates. However, the Fusidic acid precipitate is difficult to process into a cream form first due to its coarse and uneven particle size and second retrieving Fusidic acid from wet cake involves drying and further handling which deteriorates the Fusidic acid due to exposure to oxygen
- The stability of the API in a Fusidic acid cream is unreliable due to the thermolabile nature of Fusidic acid Stabilization of medicaments containing Fusidic acid against oxidation involves observing a number of stringent precautionary procedures during manufacture and storage. These include:
- replacing Oxygen in pharmaceutical containers with inert gases such as Nitrogen, Carbon dioxide, Helium and the like
- avoiding contact of the medicament with heavy metal ions which catalyze oxidation,
- storing the API at reduced temperatures throughout its shelf life before processing In practice this means stricter controls during the manufacture as well as storage of such API (storing it typically at 2° C. to 8° C. in air-tight containers throughout their shelf life).

There is therefore a need to provide a process of making a Fusidic acid cream in which Fusidic acid will be of greater stability than the stability of the Fusidic acid in the conventional creams, particularly at the time of the manufacture of the cream, and which will sustain its stability at an acceptable level throughout its shelf life.

OBJECTS AND ADVANTAGES OF INVENTION

It is therefore one object of the present invention to provide a process of making a cream which contains Fusidic acid as the active API but which has greater stability of the API than the Fusidic acid manufactured using other means, throughout its shelf life.

BRIEF SUMMARY OF INVENTION

The invention discloses a process to make dermaceutical cream containing Fusidic acid which is formed in situ from Sodium Fusidate as the starting raw material, wherein Sodium Fusidate is converted into Fusidic acid under oxygen-free environment created using inert gas, preferably nitrogen. The cream produced by the process of the present invention has greater shelf-life stability and the finer particle size of the API than the conventional creams containing Fusidic acid. The cream produced by the process of the present invention contains Fusidic acid as the API that has been formed in situ from Sodium Fusidate, in a cream base comprising a preservative, an acid, a co-solvent, an emulsifier and a waxy material along with water, preferably purified water. The cream produced by the process of the present invention further optionally contains an ingredient selected from a group comprising, a buffering agent, an anti oxidant, a chelating agent, and a humectant, or any combination thereof.

DETAILED DESCRIPTION OF INVENTION

We discussed earlier the known aspects of the topical preparations that have Fusidic acid and Sodium Fusidate as the APIs. It is evident from the current state of knowledge that:
- Creams containing Fusidic acid that is made using Sodium Fusidate as starting API are not available.
- There is no published data on the stability of Sodium Fusidate as the API.
- Sodium Fusidate is not considered to be inherently more stable as an API than Fusidic acid.

In the face of this, it has been surprisingly discovered that Sodium Fusidate as an API is significantly more stable than Fusidic acid and that Fusidic acid deteriorates more rapidly than Sodium Fusidate.

There is no published data on the stability of Sodium Fusidate as the API. The applicant carried out experiments on Sodium Fusidate to evaluate its stability. It can be seen from Table 2 that the degradation of Sodium Fusidate over a temperature range of room temperature to 45° C. ranged between 2.45% and 6%.

Tables 1 and 2 also show the comparison between the stability of the Fusidic acid and Sodium Fusidate as raw APIs. The study was carried out using an in-house HPLC method developed by the applicant, which the applicant believes is a true stability-indicating method as opposed to the titration method suggested in British Pharmacopoeia (BP). This is because the BP method does not differentiate between the intact API and the degraded form.

Stability Analysis of Fusidic Acid:

TABLE 1

Results Of 3-Month-Old Fusidic Acid (API) Analysis By Stability Indicating HPLC Method And Titration Method

| S. No | Conditions | *Initial (%) | Fusidic Acid Assay (%) | | Percentage Drop (%) | | Remarks |
|---|---|---|---|---|---|---|---|
| | | | Titration | HPLC | Titration | HPLC | |
| 1 | RT (Open) | 100.6 | 99.21 | 92.93 | 1.39 | 7.67 | API |
| 2 | RT (Closed) | | 99.02 | 94.37 | 1.58 | 6.23 | analysed |
| 3 | 45° C. (Open) | | 98.52 | 89.52 | 2.08 | 11.08 | After 3 |
| 4 | 45° C. (Closed) | | 99.10 | 92.12 | 1.50 | 8.48 | Months |

Name of the Sample: FUSIDIC ACID BP
Pack: Open & Closed Petri dish

Stability Analysis of Sodium Fusidate:

TABLE 2

Results Of 3 Months Old Sodium Fusidate (API) Analysis By Stability Indicating HPLC Method And Titration Method

| S. No | Conditions | *Initial (%) | Sodium Fusidate Assay (%) | | Percentage (%) | | Remarks |
|---|---|---|---|---|---|---|---|
| | | | Titration | HPLC | Titration | HPLC | |
| 1 | RT (Open) | 98.7 | 97.71 | 96.25 | 0.99 | 2.45 | API |
| 2 | RT (Closed) | | 98.85 | 97.67 | −0.15 | 1.03 | analysed |
| 3 | 45° C. (Open) | | 97.07 | 92.65 | 1.63 | 6.05 | After 3 |
| 4 | 45° C. (Closed) | | 97.16 | 92.96 | 1.54 | 5.74 | Months |

Name of the Sample: Sodium Fusidate BP
Pack: Open & Closed Petri dish

In both studies the * Initial denotes the results of the samples tested at the time of receipt of the API from the supplier.

It can be observed from Tables 1 and 2 that:
In the case of Fusidic Acid, there is about 7.7% loss in 3 Months at room temperature (open condition) and about 11% loss in 3 Months at 45° C. (open condition).
In the case of Sodium Fusidate, there is about 2.5% loss in 3 Months at room temperature (open condition) and about 6% loss in 3 Months at 45° C. (open condition).

The data thus shows that Sodium Fusidate as an API is more stable than Fusidic acid.

The applicants explored the possibility of making a cream (rather than an ointment) using Sodium Fusidate (rather than Fusidic acid). Although Sodium Fusidate has been used in dermaceutical applications, it has not been possible to make creams that use Sodium Fusidate. This is because of the inherent alkalinity of Sodium Fusidate (pH 7.5 to 9), which means it cannot be used in a cream form therefore all products manufactured using Sodium Fusidate as starting material are ointments. A dermaceutical cream that uses Sodium Fusidate would exploit the benefit of the fact that Sodium Fusidate is more stable than Fusidic acid and it would also provide a cream formulation which is far superior in its application qualities than an ointment. It would thus fill an existing need for a cream that has better stability than currently available creams containing Fusidic acid.

The applicant therefore surprisingly discovered that in order to achieve greater stability of the API in a dermaceutical cream, Sodium Fusidate rather than Fusidic acid may be used as the starting API during the cream's manufacture. Using Sodium Fusidate as starting material eliminates the drawback associated with the manufacture and storage of existing Fusidic acid creams.

The applicant has also discovered that the Fusidic acid cream prepared using Sodium Fusidate as the staring API shows good chemical stability, efficacy, and microbial sensitivity.

The application discloses a process of making a cream containing Fusidic acid (the API) that has been prepared using Sodium Fusidate as the starting API, in which Fusidic acid forms in-situ under totally oxygen-free environment created using inert gas, preferably nitrogen, by slow addition of an acid, into a molecular dispersion form (due to the presence of a co-solvent) at the intermediate stage, and which Fusidic acid regenerates as an extremely fine dispersion when added to a final cream base, thereby resulting in a finely and homogeneously dispersed Fusidic acid in the final cream. All these operations are performed in an environment free of atmospheric oxygen created using inert gas, preferably nitrogen. The cream made using the process of the present invention contains Fusidic acid as the API that has been formed in situ from Sodium Fusidate, in a cream base comprising a buffering agent, a preservative, an acid, a co-solvent, an emulsifier and a waxy material along with water, preferably purified water.

The APIs which may be employed in the process of the present invention as starting APIs are either acid-based actives or their salts well known in the art of treating bacterial primary and secondary infections. Examples of suitable acid-based actives or their salts which may be used include, but are not limited to Sodium Fusidate.

These acid-based active compounds or their salts require a base component to be used in the pharmaceutical composition that uses the compounds, since the compounds cannot, by themselves, be deposited directly on to human skin due to their harshness.

The cream base of the cream made using the process of the present invention optionally further comprises an ingredient selected from a group comprising an anti oxidant, a chelating agent, and a humectant, or any combination thereof.

The present invention provides a process to make a novel cream that has been produced using Sodium Fusidate as the starting raw material, and which cream contains Fusidic acid of high therapeutic efficacy and of chemical stability that is generally superior to the commercially available creams containing Fusidic acid.

The Fusidic acid cream made using the process of the present invention has been manufactured in a totally oxygen free environment under purging with inert gas and applying vacuum, the inert gas being preferably nitrogen. Under these conditions, the Sodium Fusidate is converted in situ into Fusidic acid. The cream of the present invention is used in the treatment of bacterial skin infections.

Details of the Process of Manufacturing the Novel Sodium Fusidate Cream

Preferred Embodiment 1

The preferred embodiment of the invention discloses a process to make a dermaceutical cream containing Fusidic acid, said process comprising the step of using sodium fusidate as the raw API and converting it in situ into Fusidic acid under oxygen-free environment in a cream base.

Embodiment No. 2

In an embodiment of the present invention the process of making the composition is disclosed, wherein the step of converting the sodium fusidate in situ into Fusidic acid of the preferred embodiment comprises the steps of:
  a. heating purified water in the range from 20% (w/w) to 75% (w/w), preferably 35% (w/w) to 50% (w/w), more preferably 40% (w/w) to 43% (w/w) in a water-phase vessel to 70° C. to 80° C.,
  b. adding to said water-phase vessel a preservative, selected from a group comprising Methylparaben, Propylparaben, Chlorocresol, Potassium sorbate, Benzoic acid and the like, either singly or any combination thereof, in an amount between 0.05% (w/w) to 0.5% (w/w), preferably 0.3% (w/w), more preferably 0.2% (w/w), more preferably Benzoic acid,
  c. mixing the mixture using an agitator at 10 to 50 RPM while maintaining the temperature of the mixture at 70° C. to 80° C.,
  d. adding waxy materials, selected from a group comprising White soft paraffin, Liquid Paraffin, Hard paraffin and the like, either singly or any combination thereof, in an amount between 5% (w/w) to 20% (w/w), preferably 15% (w/w), more preferably 12.5% (w/w), to an oil-phase vessel and melting said wax by heating to 70° C. to 80° C.,
  e. adding to said oil-phase vessel a primary emulsifier, preferably in the form of a non ionic Surfactant, selected from a group comprising Cetostearyl alcohol, Cetomacrogol-1000, either singly or any combination thereof, preferably Cetostearyl alcohol in an amount between 1% (w/w) to 15% (w/w), preferably 15% (w/w), more preferably 12.5% (w/w), and optionally a secondary emulsifier selected from a group comprising Polysorbate-80, Span-80 and the like, preferably Polysorbate-80, in an amount between 1 to 5% w/w, more preferably 2% w/w and mixing the mixture thoroughly, preferably using an agitator, at 10 to 50 RPM while maintaining the temperature of the mixture at 70° C. to 80° C.,
  f. transferring under vacuum in the range of minus 1000 to minus 300 mm of mercury and at 70° C. to 80° C. the contents of the water-phase and oil-phase vessels to a mixing vessel and mixing the mixture thoroughly, preferably using an agitator, at 10 to 50 RPM to form an emulsion,
  g. cooling said emulsion to 45° C. preferably by circulating cold water, preferably at 8° C. to 15° C. from a cooling tower in the jacket of the mixing vessel,
  h. in an API-vessel adding a co-solvent, selected from a group comprising Propylene Glycol, Hexylene Glycol, PolyEthylene Glycol-400 and the like, either singly or any combination thereof, in an amount between 5% (w/w) to 40% (w/w), preferably 30% (w/w), more preferably 25% (w/w), preferably propylene glycol, subjecting the contents of said API-vessel to inert gas flushing, said inert gas being preferably nitrogen, and adding sodium fusidate to the mixture, said sodium fusidate added in an amount between 0.1% (w/w) to about 25% (w/w), preferably from about 0.5% (w/w) to about 5% (w/w) and more preferably about 2.08% (w/w), and dissolving said Sodium Fusidate in the mixture,
  i. adjusting the pH of the mixture in the API-vessel of step h to below 2 by using an acid, selected from a group comprising acids such as HCl, H2So4, HNO3, Lactic acid and the like, either singly or any combination thereof, preferably Nitric acid to form a proportion from about 0.005% (w/w) to 0.5% (w/w), preferably 0.3% (w/w), more preferably 0.25% (w/w),
  j. transferring the contents of the API-vessel of step i to the mixing vessel of step g with continuous stirring at 10 to 50 RPM and homogenizing the mixture at 1000 to 3000 RPM under inert gas flushing and under vacuum of minus 1000 to minus 300 mm of mercury, said inert gas being preferably nitrogen,
  k. cooling the contents of the mixing vessel of step j to 30° C. to 37° C. using circulation of cooled water from a cooling tower at 8° C. to 15° C. into the jacket of mixing vessel,
  l. turning off the agitator and the homogenizer and removing the mixture of the Mixing vessel of step k to a storage container.

Embodiment No. 2

In an embodiment of the present invention, the co-solvent of step h of the embodiment no. 1 above also serves as a humectant. However, in another embodiment of the invention, an additional humectant may be added, selected from a group comprising Glycerin, Sorbitol, Propylene glycol and the like, either singly or any combination thereof, to form a proportion from about 5% (w/w) to 40% (w/w), preferably 30% (w/w), more preferably 25% (w/w).

Embodiment No. 3

In another embodiment of the present invention the process described in embodiment no. 2 further incorporates adding a chelating agent, selected from a group comprising Disodium EDTA and the like, either singly or any combination thereof, to form a proportion from about 0.01% (w/w) to 1% (w/w), preferably 0.5% (w/w), more preferably 0.1% (w/w).

Embodiment No. 4

In yet another embodiment of the present invention the process described in embodiments no. 2 and 3 further incorporate a buffering agent selected from a group comprising Di Sodium Hydrogen Ortho Phosphate, Sodium Hydrogen Ortho Phosphate and the like from about 0.01% (w/w) to 1.00% (w/w), preferably 0.5% (w/w), more preferably 0.05% (w/w).

Embodiment No. 5

In a further embodiment of the present invention the process described in embodiments no. 2 to 4 further incorporate an anti oxidants selected from a group comprising Butylated Hydroxy Anisole, Butylated Hydroxy Toluene and the like from about 0.001% (w/w) to 5% (w/w), preferably 0.1% (w/w), more preferably 0.01% (w/w).

Embodiment No. 6

Yet another process of making the composition as per the preferred embodiment is disclosed, said process comprises the steps of:
a. heating purified water in the range from 20% (w/w) to 75% (w/w), preferably 35% (w/w) to 50% (w/w), more preferably 40% (w/w) to 43% (w/w) in a water-phase vessel to 70° C. to 80° C.,
b. adding to said water-phase vessel a preservative, selected from a group comprising Methylparaben, Propylparaben, Chlorocresol, Potassium sorbate, Benzoic acid and the like, either singly or any combination thereof, in an amount between 0.05% (w/w) to 0.5% (w/w), preferably 0.3% (w/w), more preferably 0.2% (w/w), more preferably Benzoic acid,
c. adding to said water-phase vessel of step b, a chelating agent, selected from a group comprising Disodium EDTA and the like, either singly or any combination thereof, in an amount between 0.01% (w/w) to 1% (w/w), preferably 0.5% (w/w), more preferably 0.1% (w/w),
d. adding to said water-phase vessel of step c, a buffering agent selected from a group comprising Di Sodium Hydrogen Ortho Phosphate, Sodium Hydrogen Ortho Phosphate and the like in an amount between 0.01% (w/w) to 1.00% (w/w), preferably 0.5% (w/w), more preferably 0.05% (w/w).
e. mixing the mixture of step d using an agitator at 10 to 50 RPM while maintaining the temperature of the mixture at 70° C. to 80° C.,
f. adding waxy materials, selected from a group comprising White soft paraffin, Liquid Paraffin, Hard paraffin and the like, either singly or any combination thereof, in an amount between 5% (w/w) to 20% (w/w), preferably 15% (w/w), more preferably 12.5% (w/w), to an oil-phase vessel and melting said wax by heating to 70° C. to 80° C.,
g. adding to said oil-phase vessel of step f, a primary emulsifier, preferably in the form of a non ionic Surfactant, selected from a group comprising Cetostearyl alcohol, Cetomacrogol-1000, either singly or any combination thereof, preferably Cetostearyl alcohol in an amount between 1% (w/w) to 15% (w/w), preferably 15% (w/w), more preferably 12.5% (w/w), and optionally a secondary emulsifier selected from a group comprising Polysorbate-80, Span-80 and the like, preferably Polysorbate-80, preferably in an amount between 1 to 5% w/w, more preferably 2% w/w and mixing the mixture thoroughly, preferably using an agitator, at 10 to 50 RPM while maintaining the temperature of the mixture at 75° C.+/−5° C.,
h. transferring under vacuum in the range of minus 1000 to minus 300 mm of mercury and at 75° C.+/−5° C. the contents of the water-phase and oil-phase vessels to a mixing vessel and mixing the mixture thoroughly, preferably using an agitator, at 10 to 50 RPM to form an emulsion,
i. cooling said emulsion to 45° C. preferably by circulating cold water, preferably at 8° C. to 15° C. from a cooling tower in the jacket of the mixing vessel,
j. in an API-vessel adding a co-solvent, selected from a group comprising Propylene Glycol, Hexylene Glycol, PolyEthylene Glycol-400 and the like, either singly or any combination thereof, in an amount between 5% (w/w) to 40% (w/w), preferably 30% (w/w), more preferably 25% (w/w), preferably propylene glycol, and dissolving an antioxidant, selected from a group comprising Butylated Hydroxy Anisole, Butylated Hydroxy Toluene and the like, either singly or any combination thereof, in an amount between 0.001% (w/w) to 5% (w/w), preferably 0.1% (w/w), more preferably 0.01% (w/w), preferably Butylated Hydroxy Toluene in said glycol by continuous mixing,
k. subjecting the contents of said API-vessel to inert gas flushing, said inert gas being preferably nitrogen, and adding Sodium Fusidate to the mixture said sodium fusidate being added in an amount between 0.1% (w/w) to about 25% (w/w), preferably from about 0.5% (w/w) to about 5% (w/w) and more preferably about 2.08% (w/w), and dissolving said Sodium Fusidate in the mixture,
l. adjusting the pH of the mixture in the API-vessel of step k to below 2 by using an acid, selected from a group comprising acids such as HCl, H2So4, HNO3, Lactic acid and the like, either singly or any combination thereof, preferably Nitric acid in an amount between 0.005% (w/w) to 0.5% (w/w), preferably 0.3% (w/w), more preferably 0.25% (w/w),
m. transferring the contents of the API-vessel of step l to the mixing vessel of step i with continuous stirring at 10 to 50 RPM and homogenizing the mixture at 1000 to 3000 RPM under inert gas flushing and under vacuum of minus 1000 to minus 300 mm of mercury, said inert gas being preferably nitrogen, n. cooling the contents of the mixing vessel of step m to 30° C. to 37° C. using circulation of cooled water from a cooling tower at 8° C. to 15° C. into the jacket of mixing vessel o. turning off the agitator and the homogenizer and removing the mixture of said mixing vessel of step n to a storage container.

The co-solvent of step i also serves as a humectant. However, in an embodiment of the invention, an additional humectant may be added, selected from a group comprising Glycerin, Sorbitol, Propylene glycol and the like, either singly or any combination thereof, to form a proportion from about 5% (w/w) to 40% (w/w), preferably 30% (w/w), more preferably 25% (w/w).

The cream obtained using the process of the present invention is homogenous and white to off white in colour and viscous in consistency. The pH of the product made using the process of the present invention is from about 3 to 6. On the other hand, Sodium Fusidate ointments that are commercially available are greasy and cosmetically non elegant.

It is essential that the active drug penetrates the skin for the optimum bio-dermal efficacy. The particle size of the active drug plays an important role here. It is necessary that the active drug is available in a finely dispersed form for the product to be being efficacious. Also this is to be achieved in the safe pH compatible environment of skin (4.0 to 6.0). To achieve all these, it is essential to choose proper vehicles or co-solvents for the dissolution or dispersion of the drug.

Particle size analysis was carried out on the cream made using the process of the present invention and on some commercially available product samples (samples A, C, D, F, G, and K). Maximum and minimum particle sizes, mean particle size and standard deviation and the coefficient of variation were assessed.

TABLE 3

| | Minimum Particle Size (μm) | Maximum Particle Size (μm) | Mean Particle Size (μm) | Standard Deviation | Coefficient of Variation |
|---|---|---|---|---|---|
| Present Invention | 2.33 | 16.30 | 10.01 | 3.982 | 0.397 |
| A | 7.23 | 39.58 | 18.09 | 9.251 | 0.511 |
| C | 6.07 | 32.69 | 14.11 | 6.692 | 0.474 |
| D | 9.8 | 27.52 | 18.48 | 4.98 | 0.269 |
| F | 7.93 | 19.90 | 14.82 | 4.033 | 0.272 |
| G | 7.29 | 29.48 | 15.25 | 6.065 | 0.398 |
| K | 5.75 | 32.63 | 16.80 | 8.112 | 0.483 |

The particle size distribution analysis clearly indicates the presence of Fusidic acid of fine particle size in the product of the present invention, the size that is advantageously much reduced than the conventional products. This is attributed to the fact that the instant product is made using Sodium Fusidate using in situ conversion of Sodium Fusidate to Fusidic acid in a finely dispersed form. All of the measured parameters are better than those found for the commercially available creams containing Fusidic acid. This is another clear advantage of the product disclosed herein over the commercially available products.

The product of the present invention is efficacious due to the pronounced antibacterial activity of the regenerated Fusidic acid which is available in reduced particle size than the conventional products, and in a finely dispersed form.

The inventor has screened different co-solvents such as Propylene Glycol, Hexylene Glycol, PolyEthyleneGlycol-400 & the like and dissolved the Sodium Fusidate in one of above co-solvents varying from about 5% (w/w) to 40% (w/w) under inert gas purging and under vacuum and converted to Fusidic acid in-situ by adding an acid such as HCl, $H_2SO_4$, $HNO_3$, Lactic acid and the like from about 0.005% (w/w) to about 0.5% (w/w) under stirring and obtained Fusidic acid in more stabilized and solution form, which makes our final product in a cream base which easily penetrates the skin and highly efficacious, and also highly derma compatible by having a pH of about 3.0 to about 6.0.

The stability of the product is confirmed by the stability studies performed for 6 months as per ICH guidelines and a comparison of stress studies done for in-house product with those on samples of commercially available comparable products.

Experimental Data

API-stability experiments were carried out (see tables 4-9) using the product of the present invention and products currently commercially available. Tests were carried out to observe (or measure as appropriate) the physical appearance of the product, the pH value and assay of the API over a period of time. Tests were also carried out to assess the stability by subjecting the product to stress studies such as autoclave test and oxydative degradation test. Further, in vitro antimicrobial zone of inhibition studies were also carried out over a period of time. Each gram of product of the present invention used for the tests contained Sodium Fusidate in the amount required to produce 2% (w/w) Fusidic acid in the finished product.

The product used for the Stability Studies, Autoclave and Oxydative degradation tests contained approximately 10% extra API (overages). The product of the present invention used for studies contained Fusidic acid cream prepared using Sodium Fusidate as starting material. It was packaged in an aluminium collapsible tube and each gram of the product contained 20.8 mg of Sodium Fusidate (in conformance with BP), which is equivalent to 20 mg of Fusidic acid (BP conformant). The details of the analyses on commercially available comparable products (Fusidic Acid creams) are provided in the tables 13-A and 14 as appropriate.

TABLE 4

Description Test, Batch No. ASF-09

| Conditions | Initial | $1^{st}$ Month | $2^{nd}$ Month | $3^{rd}$ Month | $6^{th}$ Month |
|---|---|---|---|---|---|
| 40° C. 75% RH | Homogenous White to off White viscous cream | Best possible value | Best possible value | Best possible value | Best possible value |
| 30° C. 65% RH | | Do | Do | Do | Do |
| 25° C. 60% RH | | Do | Do | Do | Do |
| Temperature cycling | | Do | — | — | — |
| Freezthaw | | Do | — | — | — |

Measured parameter: Physical appearance
Best possible value of measured parameter: Homogeneous White to off White Viscous cream
Method of measurement: Observation by naked eye

TABLE 5 pH Test, Batch No. ASF-09

| Conditions | Initial | $1^{st}$ Month | $2^{nd}$ Month | $3^{rd}$ Month | $6^{th}$ Month |
|---|---|---|---|---|---|
| 40° C. 75% RH | 4.22 | 4.21 | 4.22 | 4.20 | 4.19 |
| 30° C. 65% RH | | 4.20 | 4.21 | 4.21 | 4.20 |
| 25° C. 60% RH | | 4.21 | 4.21 | 4.20 | 4.19 |

TABLE 5-continued pH Test, Batch No. ASF-09

| Conditions | Initial | 1st Month | 2nd Month | 3rd Month | 6th Month |
|---|---|---|---|---|---|
| Temperature cycling | | 4.22 | — | — | — |
| Freezthaw | | 4.21 | — | — | — |

Measured parameter: pH
Limits of measured parameter: 3-6
Method of measurement: Digital pH Meter

TABLE 6

Assay (%) Test, Batch No. ASF-09

| Conditions | Initial | 1st Month | 2nd Month | 3rd Month | 6th Month |
|---|---|---|---|---|---|
| 40° C. 75% RH | 108.60 | 108.56 | 108.26 | 108.11 | 108.05 |
| 30° C. 65% RH | | 108.53 | 108.36 | 108.26 | 108.11 |
| 25° C. 60% RH | | 108.59 | 108.45 | 108.39 | 108.26 |
| Temperature cycling | | 107.53 | — | — | — |
| Freezthaw | | 108.01 | — | — | — |

Measured parameter: Assay (%)
Limits of measured parameter: 90-110%
Method of measurement: HPLC Method It is apparent from tables 4-6 that on all counts, the pH value, the physical appearance, and stability, the product of the present invention is quite good.

Table 7 provides reference dates for samples A-I which were taken from commercially available creams of Fusidic acid and used for analyses.

TABLE 7

| Sample Number | Mfg. Date | Exp. Date |
|---|---|---|
| Present invention | October 2009 | September 2011 |
| Sample A | August 2009 | July 2011 |
| Sample B | August 2009 | July 2011 |
| Sample C | July 2009 | June 2011 |
| Sample D | July 2009 | June 2011 |
| Sample E | August 2009 | July 2011 |
| Sample F | August 2009 | July 2011 |
| Sample G | August 2009 | July 2011 |
| Sample H | July 2009 | June 2011 |
| Sample I | December 2009 | November 2011 |

TABLE 8

Autoclave Analysis (%) Test,

| Sr. No | Name of the Products and Details | Analysis-I (%) | | | Analysis-II (%) | | | Average drop of Analysis-I & Analysis-II (%) |
|---|---|---|---|---|---|---|---|---|
| | | Initial | After Autoclave | Drop in % | Initial | After Autoclave | Drop in % | |
| 1 | Present invention | 110.47 | 104.61 | 5.86 | 110.62 | 104.86 | 5.76 | 5.81 |
| 2 | Sample A | 101.81 | 91.79 | 10.02 | 100.93 | 91.65 | 9.28 | 9.65 |
| 3 | Sample B | 92.69 | 83.54 | 9.15 | 91.13 | 83.08 | 8.05 | 8.6 |
| 4 | Sample C | 110.47 | 98.56 | 11.91 | 110.2 | 99.21 | 10.99 | 11.45 |
| 5 | Sample D | 101.3 | 94.84 | 6.46 | 102.13 | 94.65 | 7.48 | 6.97 |
| 6 | Sample E | 100.99 | 94.51 | 6.48 | 100.21 | 93.51 | 6.70 | 6.59 |
| 7 | Sample F | 96.33 | 84.15 | 12.18 | 95.88 | 85.12 | 10.76 | 11.47 |
| 8 | Sample G | 104.75 | 93.19 | 11.56 | 103.25 | 93.12 | 10.13 | 10.84 |
| 9 | Sample H | 101.26 | 88.35 | 12.91 | 100.86 | 87.98 | 12.88 | 12.89 |
| 10 | Sample I | 101.58 | 87.06 | 14.52 | 100.61 | 88.01 | 12.6 | 13.56 |

Measured parameter: Assay (%)
Limits of measured parameter: 90-110%
Method of measurement: HPLC Method

TABLE 9

Oxidative degradation Analysis (%) Test,

| Sr. No | Name of the Products and Details | Analysis(%) | | |
|---|---|---|---|---|
| | | Initial | After Oxidation | Degradation in % |
| 1 | Present invention | 110.47 | 106.75 | 3.72 |
| 2 | Sample A | 101.81 | 95.63 | 6.18 |
| 3 | Sample B | 92.69 | 83.15 | 9.54 |
| 4 | Sample C | 110.47 | 101.93 | 8.54 |
| 5 | Sample D | 101.3 | 93.25 | 8.05 |
| 6 | Sample E | 100.99 | 95.47 | 5.52 |
| 7 | Sample F | 96.33 | 90.70 | 5.63 |
| 8 | Sample G | 104.75 | 96.46 | 8.29 |
| 9 | Sample H | 101.26 | 94.53 | 6.73 |
| 10 | Sample I | 101.58 | 88.92 | 12.66 |

Measured parameter: Assay (%)
Limits of measured parameter: NA
Method of measurement: HPLC Method Inference from Table 8:

The assay results of Autoclave analysis (121° C. applied for 15 Minutes) indicate that the commercially available samples of Fusidic acid cream (Sr. Nos. 2-10) show more percentage drop in API content than for the product of the present invention (Sr. no. 1).

Inference from Table 9:

The above Assay results of Oxidative degradation analysis (30% Hydrogen peroxide Solution over a period of 12 hours) indicate that the various Market samples of Fusidic acid cream (Sr. Nos. 2-10) show significantly higher API degradation (indicated by the percentage drop in API content) than for the product of the present invention (Sr. no. 1).

From the above data, it is evident that product of the present invention is quite stable at ambient conditions and also at elevated temperature & humid conditions of storage. Also the autoclave studies & Oxidative degradation studies further confirm the stability of the product. This is a major advantage over the currently available Fusidic acid creams. The stability of the product is further ascertained by the shelf-life prediction of the formulation using arrhenius plot of degradation employing Nova-LIMS software.

The antimicrobial/antibacterial activity of the product is confirmed by the in vitro Antimicrobial Zone of Inhibition studies for the product against *Staphylococcus aureus*. The details of the studies are detailed below in Table 15.

TABLE 10

| S. No | Sample | Dose | Zone Diameter Range (mm) | Inference |
|---|---|---|---|---|
| 1 | Reference standard (Fusidic acid) | 10 mcg | 21-33 | Sensitive |
|  |  | 20 mcg | 20-30 | Sensitive |
|  |  | 50 mcg | 25-32 | Sensitive |
| 2 | Positive control (Penicillin G) | 10 Units | 21-27 | Resistant |
| 3 | Negative control (DMSO 1%) | NA | NIL | NIL |
| 4 | Sample (Test Substance) (ASF-product of the present invention 2%) | 10 mcg | 21-23 | Sensitive |
|  |  | 20 mcg | 24-26 | Sensitive |
|  |  | 50 mcg | 21-24 | Sensitive |

From the above data it is evident that the product has adequate antimicrobial/antibacterial activity to treat primary and secondary bacterial infections.

The composition of the final cream is given in the table 11 below.

TABLE 11

| S. No | Ingredients | Specification | Qtty For 350 Kg | UOM | % w/w |
|---|---|---|---|---|---|
| 1 | Sodium Fusidate | BP | 7.28 | Kg | 2.08 |
| 2 | Cetostearyl Alcohol | IP | 43.75 | Kg | 12.5 |
| 3 | White Soft Paraffin | IP | 43.75 | Kg | 12.5 |
| 4 | Polysorbate 80 | IP | 7.0 | Kg | 2 |
| 5 | Propylene Glycol | IP | 87.5 | Kg | 25 |
| 6 | Benzoic Acid | IP | 0.7 | Kg | 0.2 |
| 7 | Butylated Hydroxy Toluene | IP | 0.035 | Kg | 0.01 |
| 8 | Disodium Edetate | IP | 0.35 | Kg | 0.1 |
| 9 | 1M Nitric Acid solution | IP | 14.0 | Lit | 4 |
| 10 | Disodium hydrogen orthophosphate | IP | 0.175 | Kg | 0.05 |
| 11 | Purified Water | IP | 145.46 | Kg | 41.56 |

While the above description contains much specificity, these should not be construed as limitation in the scope of the invention, but rather as an exemplification of the preferred embodiments thereof. It must be realized that modifications and variations are possible based on the disclosure given above without departing from the spirit and scope of the invention. Accordingly, the scope of the invention should be determined not by the embodiments illustrated, but by the appended claims and their legal equivalents.

We claim:

1. A process to make fusidic acid cream, said process comprising the step of using sodium fusidate as the raw active pharmaceutical ingredient and converting said sodium fusidate in situ into fusidic acid under an oxygen-free environment in a cream base.

2. A process to make fusidic acid cream as claimed in claim 1, wherein said cream base comprises a preservative, an acid, a co-solvent, an emulsifier and a waxy material along with purified water.

3. A process to make fusidic acid cream as claimed in claim 2 wherein said step of using sodium fusidate as the raw active pharmaceutical ingredient and converting said sodium fusidate in situ into fusidic acid under an oxygen-free environment in a cream base comprises the steps of:

(a) heating purified water in the range from 20% (w/w) to 75% (w/w) in a water-phase vessel to 70° C. to 80° C., (b) adding to said water-phase vessel a preservative, selected from a group consisting of methylparaben, propylparaben, chlorocresol, potassium sorbate, and benzoic acid, either singly or any combination thereof in an amount between 0.05% (w/w) to 0.5% (w/w), (c) mixing the mixture using an agitator at 10 to 50 RPM while maintaining the temperature of the mixture at 70° C. to 80° C., (d) adding waxy materials, selected from a group consisting of white soft paraffin, liquid paraffin, and hard paraffin, either singly or any combination thereof, in an amount between 5% (w/w) to 20% (w/w), to an oil-phase vessel and melting said wax by heating to 70° C. to 80° C., (e) adding to said oil-phase vessel a primary emulsifier, said primary emulsifier being in the form of a non ionic surfactant, selected from a group consisting of cetostearyl alcohol cetomacrogol-1000, either singly or any combination thereof, in an amount between 1% (w/w) to 15% (w/w), and optionally a secondary emulsifier selected from a group consisting of polysorbate-80 and span-80, in an amount between 1 to 5% w/w, and mixing the mixture thoroughly using an agitator, at 10 to 50 RPM while maintaining the temperature of the mixture at 70° C. to 80° C., (f) transferring under vacuum in the range of minus 1000 to minus 300 mm of mercury and at 70° C. to 80° C. the contents of the water-phase and oil-phase vessels to a mixing vessel and mixing the mixture thoroughly using an agitator, at 10 to 50 RPM to form an emulsion, (g) cooling said emulsion to 45° C. by circulating cold water of a temperature, 8° C. to 15° C. from a cooling tower in the jacket of the mixing vessel, (h) in an API-vessel adding a co-solvent, selected from a group consisting of propylene glycol, hexylene glycol, and polyethylene glycol-400, either singly or any combination thereof in an amount between 5% (w/w) to 40% (w/w), subjecting the contents of said API-vessel to inert gas flushing, adding sodium fusidate in an amount between 0.1% (w/w) to about 25% (w/w), and dissolving said sodium fusidate in the mixture, (i) adjusting the pH of the mixture in the API-vessel of step (h) to below 2 by using an acid, selected from a group consisting of hydrochloric acid, sulfuric acid, nitric acid and lactic acid, either singly or any combination thereof, to form a proportion from about 0.005% (w/w) to 0.5% (w/w), (j) transferring the contents of the API-vessel of step (i) to the mixing vessel of step (g) with continuous stirring at 10 to 50 RPM and homogenizing the mixture at 1000 to 3000 RPM under inert gas flushing and under vacuum of minus 1000 to minus 300 mm of mercury, (k) cooling the contents of the mixing vessel of step (j) to 30° C. to 37° C. using circulation of cooled water from a cooling tower at 8° C. to 15° C. into the jacket of mixing vessel, and (l) turning off the agitator and the homogenizer and removing the mixture of the mixing vessel of step (k) to a storage container.

4. A process to make fusidic acid cream as claimed in claim 3 further wherein a humectant is added to the mixing vessel of said step (a) in claim 3 said humectant being selected from a group consisting of glycerin, sorbitol, and propylene glycol, either singly or any combination thereof, to form a proportion from about 5% (w/w) to 40% (w/w).

5. A process to make fusidic acid cream as claimed in claim 4 further wherein a chelating agent is added to said step (a), said chelating agent being disodium EDTA to form a proportion from about 0.01% (w/w) to 1% (w/w).

6. A process to make fusidic acid cream as claimed in claim 5 further wherein a buffering agent is added to said step (a), said buffering agent being selected from a group consisting of disodium hydrogen ortho phosphate, and sodium hydrogen ortho phosphate, from about 0.01% (w/w) to 1.00% (w/w).

7. A process to make fusidic acid cream as claimed in claim 6, further wherein an anti oxidants is added to step (h), said anti oxidant being selected from a group consisting of butylated hydroxy anisole, and butylated hydroxy toluene, from about 0.001% (w/w) to 5% (w/w).

8. A process to make fusidic acid cream as claimed in claim 1, wherein said cream base comprises a preservative, an acid, is co-solvent, an emulsifier and a waxy material along with purified water, and a further ingredient selected from a group consisting of a buffering agent, an anti oxidant, a chelating agent, and a humectant, or any combination thereof.

9. A process to make fusidic acid cream as claimed in claim 1 wherein the step of using sodium fusidate as the raw active pharmaceutical ingredient and converting said sodium fusidate in situ into fusidic acid under an oxygen-free environment in a cream base comprises the steps of:

(a) heating purified water in the range from 20% (w/w) to 75% (w/w), in a water-phase vessel to 70° C. to 80° C., (b) adding to said water-phase vessel a preservative, selected from a group consisting of methylparaben, propylparaben, chlorocresol, potassium sorbate, and benzoic acid, either singly or any combination thereof, in an amount between 0.05% (w/w) to 0.5% (w/w), (c) adding to said water-phase vessel of step (b), a chelating agent in the form of disodium EDTA in an amount between 0.01% (w/w) to 1% (w/w), (d) adding to said water-phase vessel of step (c), a buffering agent selected from a group consisting of disodium hydrogen ortho phosphate, and sodium hydrogen ortho phosphate, in an amount between 0.01% (w/w) to 1.00% (w/w), (e) mixing the mixture of step (d) using an agitator at 10 to 50 RPM while maintaining the temperature of the mixture at 70° C. to 80° C., (f) adding waxy materials, selected from a group consisting of white soft paraffin, liquid paraffin, and hard paraffin, either singly or any combination thereof, in an amount between 5% (w/w) to 20% (w/w), to an oil-phase vessel and melting said wax by heating to 70° C. to 80° C., (g) adding to said oil-phase vessel of step (f), a primary emulsifier, said primary emulsifier being in the form of a non ionic surfactant, selected from a group consisting of cetostearyl alcohol and cetomacrogol-1000, eider singly or any combination thereof, in an amount between 1% (w/w) to 15% (w/w), and optionally a secondary emulsifier selected from a group consisting of polysorbate-80, and span-80, in an amount between 1 to 5% w/w, and mixing the mixture thoroughly using an agitator, at 10 to 50 RPM while maintaining the temperature of the mixture at 75° C.+/−5° C., (h) transferring under vacuum in the range of minus 1000 to minus 300 mm of mercury and at 70° C. to 80° C. the contents of said water-phase and oil-phase vessels to a mixing vessel and mixing the mixture thoroughly, wherein the mixture is mixed using an agitator, at 10 to 50 RPM to form an emulsion, (i) cooling said emulsion to 45° C. by circulating cold water, from a cooling tower in the jacket of the mixing vessel, (j) in an API-vessel adding a co-solvent, selected from a group comprising propylene glycol, hexylene glycol, and polyethylene glycol-400, either singly or any combination thereof, in an amount between 5% (w/w) to 40% (w/w), and dissolving an antioxidant, selected from a group consisting of butylated hydroxy anisole and butylated hydroxy toluene, either singly or any combination thereof, in an amount between 0.001% (w/w) to 5% (w/w), in said glycol by continuous mixing, (k) subjecting the contents of said API-vessel to inert gas flushing, adding sodium fusidate in an amount between 0.1% (w/w) to about 25% (w/w), and dissolving said sodium fusidate in the mixture, (l) adjusting the pH of the mixture in the API-vessel of step (k) to below 2 by using an acid, selected from a group consisting of hydrochloric acid, sulfuric acid, nitric acid and lactic acid, either singly or any combination thereof, in an amount between 0.005% (w/w) to 0.5% (w/w), (m) transferring the contents of the API-vessel of step (l) to the mixing vessel of step (i) with continuous stirring at 10 to 50 RPM and homogenizing the mixture at 1000 to 3000 RPM under inert gas flushing and under vacuum of minus 1000 to minus 300 mm of mercury, (n) cooling the contents of the mixing vessel of step (m) to 30° C. to 37° C. using circulation of cooled water from a cooling tower into the jacket of mixing vessel, (o) turning off the agitator and the homogenizer and removing the mixture of said mixing vessel of step (n) to a storage container.

10. A process as claimed in claim 3 wherein
said purified water of step (a) is heated in the range from 40% (w/w) to 43% (w/w),
said preservative of step (b) is benzoic acid added in an amount of 0.2% (w/w),
said waxy material of step (d) is added in an amount of 12.5% (w/w),
said primary emulsifier of step (e) is cetostearyl alcohol added in an amount of 12.5% (w/w) and the said secondary emulsifier is polysorbate-80 added in an amount of 2% (w/w),
said emulsion of step (g) is cooled at 8° C. to 15° C.,
said co-solvent of step (h) is propylene glycol added in an amount of 25% (w/w),
said inert gas flushed in the API-vessel of step (h) is nitrogen,
said sodium fusidate of step (h) is added in an amount of 2.08 (w/w),
said acid of step (i) is nitric acid added in an amount of 0.25%,
said inert gas of step (j) is nitrogen.

11. A process to make fusidic acid cream as claimed in claim 4, wherein said humectant is added in an amount of 25% (w/w).

12. A process to make fusidic acid cream as claimed in claim 5, wherein said chelating agent is added in an amount of 0.1% (w/w).

13. A process to make fusidic acid cream as claimed in claim 6, wherein said buffering agent is added in an amount of 0.05% (w/w).

14. A process to make fusidic acid cream as claimed in claim 7, wherein said anti oxidant is added in an amount of 0.01% (w/w).

15. A process as claimed in claim 9 wherein
- said purified water of step (a) is heated in the range from 40% (w/w) to 43% (w/w),
- said preservative of step (b) is benzoic acid added in an amount of 0.2% (w/w),
- said chelating agent of step (c) is added in an amount of 0.1% (w/w),
- said buffering agent of step (d) is added in an amount of 0.05% (w/w),
- said waxy material of step (f) is added in an amount of 12.5% (w/w),
- said primary emulsifier of step (g) is cetostearyl alcohol added in an amount of 12.5% (w/w) and the said secondary emulsifier is polysorbate-80 added in an amount of 2% (w/w),
- said emulsion of step (i) is cooled at 8° C. to 15° C.,
- said co-solvent of step (j) is propylene glycol added in an amount of 25% (w/w),
- said inert gas flushed in the API-vessel of step (k) is nitrogen,
- said sodium fusidate of step (k) is added in an amount of 2.08% (w/w),
- said acid of step (l) is nitric acid added in an amount of 0.25%,
- said inert gas of step (m) is nitrogen.

* * * * *